United States Patent [19]

Walling

[11] 4,233,984
[45] Nov. 18, 1980

[54] RESPIRATORY VENTILATING DEVICE

[76] Inventor: Peter T. Walling, 14126 Brookridge Cir., Dallas, Tex. 75240

[21] Appl. No.: 920,723

[22] Filed: Jun. 30, 1978

[51] Int. Cl.³ ............................................ A61M 25/00
[52] U.S. Cl. ............................................... 128/207.14
[58] Field of Search ............... 128/208, 348, 349, 350, 128/351, 240

[56] References Cited

U.S. PATENT DOCUMENTS

| | | | |
|---|---|---|---|
| 1,696,018 | 12/1928 | Schellberg | 128/240 |
| 2,175,726 | 10/1939 | Gebauer | 138/349 B |

FOREIGN PATENT DOCUMENTS 571259  9/1977  U.S.S.R. ................................. 128/351

*Primary Examiner*—Harry N. Haroian
*Attorney, Agent, or Firm*—Hubbard, Thurman, Turner, Tucker & Glaser

[57] ABSTRACT

A surgical device is disclosed which enables selective ventilation of the lungs of a patient. The device is inserted into the patient's respiratory passages and is employed in conjunction with a conventional breathing circuit which allows ventilation of either lung alone or both lungs simultaneously by pumping life supporting gases, typically including anesthetic agents, through the tube during surgery. The device comprises an elongated flexible tube split at its proximal end into left and right tubular extensions and having a curved distal end adapted to be inserted via the patient's mouth through the trachea into the left main stem bronchus. Inflatable cuffs surrounding the tube permit the lungs to be isolated from each other and from the atmosphere. The interior of the tube is divided into left and right passageways by a septum, which is arranged such that the left lung can be ventilated through the left tubular extension, the left passageway and an orifice at the distal end of the tube, and the right lung can be ventilated through the right tubular extension, the right passageway and an orifice in the side of the tube between the cuffs. The septum comprises a thin flexible membrane having a transverse dimension roughly equal to one-half the circumference of the tube's interior surface, whereby externally applied differential pressures will cause the membrane to position itself along one side of the tube to permit utilization of virtually the entire cross-sectional area within the tube for ventilating the lung corresponding to the higher of the two externally applied pressures. Both lungs can be simultaneously ventilated using equal externally applied pressures which cause the septum membrane to return to a center position, thus providing half the cross-sectional area for each of the two passageways.

3 Claims, 7 Drawing Figures 4,233,984

RESPIRATORY VENTILATING DEVICE

The present invention pertains generally to medical and surgical instruments and particularly to respiratory intubating devices for ventilating the lungs of a patient.

Devices for selective lung ventilation by the insertion of a dual-conduit tube into the respiratory passages of a patient are known in the art. One such device is described by Gebauer in U.S. Pat. No. 2,175,726, issued on Oct. 10, 1939. Unfortunately, heretofore such devices have been somewhat limited in providing the desired gas flow due to size constraints placed on the outside diameter of the tube by the size of the patient's respiratory passages. When it is necessary to ventilate a patient using only one lung, it is desirable to do so through as large a conduit or passageway as possible in order to minimize the resistance to gas flow and thus reduce the stress on the patient as will be appreciated by those skilled in the art.

Accordingly, it is a primary object of the present invention to improve upon devices exemplified by the above referenced patent in a manner that dramatically enhances utility and performance is surgical operations. More specifically, it is an object to provide an improved tube for selectively ventilating either the right or left lung alone or both lungs together in a manner that achieves lower resistance to gas flow to and from one lung when only that lung is being ventilated, by comparison to the gas flow resistance characterized by devices of the prior art.

The novel features believed characteristic of the invention are set forth in the appended claims. The essential features of the invention, however, as well as the above and other objects and advantages will be readily understood upon consideration of the following description of a presently preferred embodiment thereof when read with the accompanying illustrations, wherein:

Figure 1:
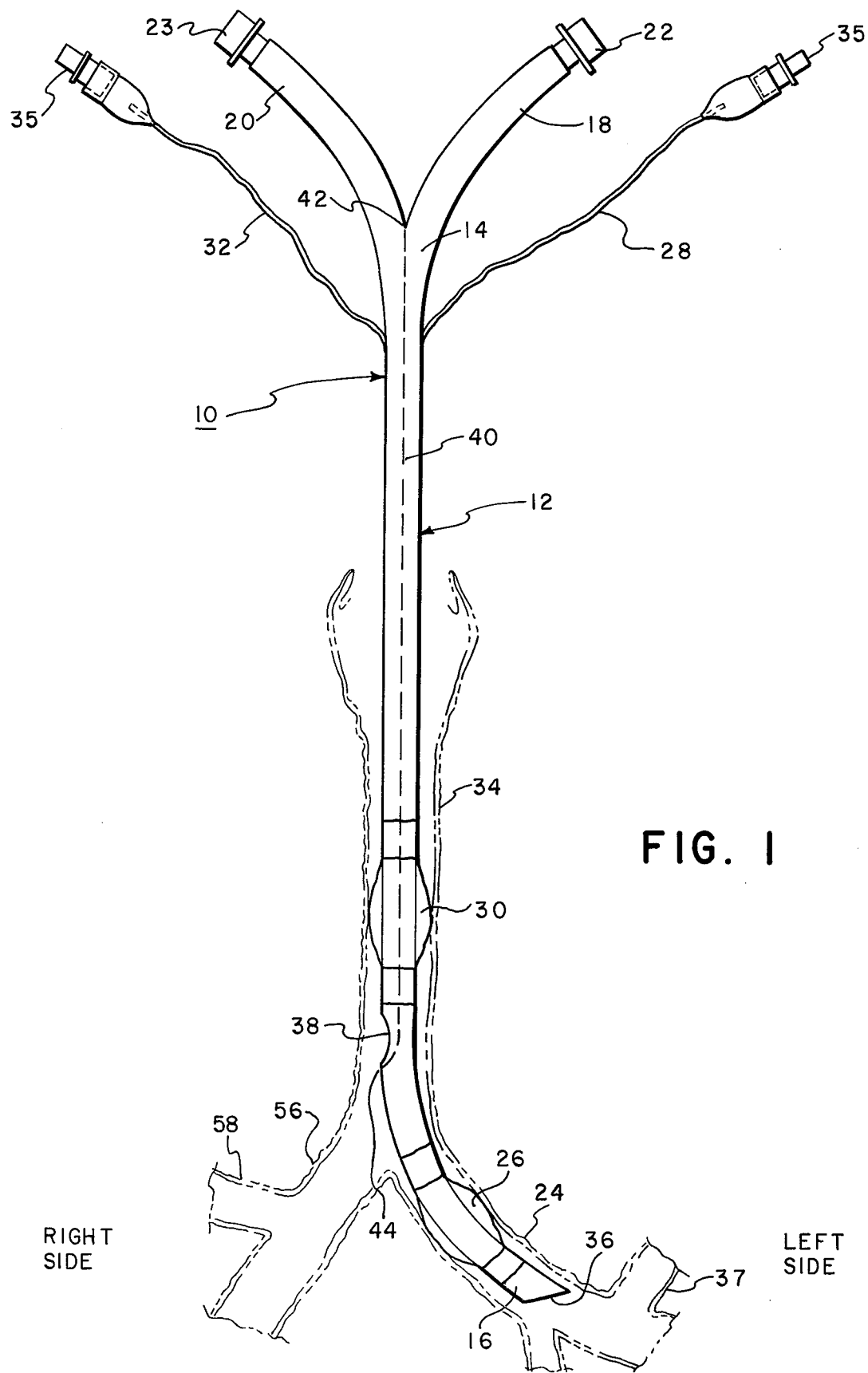
FIG. 1 is a front elevational view of a ventilating device in accordance with a preferred embodiment of the invention diagramatically illustrating its cooperation with a patient's main respiratory passages, which are shown in phantom.

With particular reference to FIG. 1, the preferred ventilating device, which is generally designated by reference numeral 10, comprises an elongated flexible tube 12 having a proximal end 14 and a distal end 16. The proximal end 14 diverges into left and right tubular extensions 18 and 20 which terminate with suitable ventilating ports 22 and 23 adapted to be connected to a conventional breathing circuit (not shown), which could be any of various mechanically or manually operable devices known to those practicing in the art. The size of the tube 12 is variable depending on the size of the patient undergoing surgery and whether the tube 12 is to be inserted through the nose or the mouth of the patient. The tube's distal end 16 is preferably curved slightly to facilitate insertion into the patient's left main stem bronchus 24 in roughly the manner depicted. A bronchial cuff 26, which is inflatable using a pilot tube 28, sealably engages the interior walls of the left main stem bronchus 24 providing gaseous isolation of the left lung from the right lung as will be appreciated by those skilled in the art. Similarly, a tracheal cuff 30, which is inflatable using a second pilot tube 32, sealably engages the interior walls of the treachea 34, to provide gaseous isolation of both lungs from the atmosphere. The pilot tubes 28 and 32 adjoin the tube 12 at the proximal end 14 and extend down within the walls of the tube 12 to their respective cuffs 26 and 30 wherein conventional openings (not shown) provide the necessary fluid communication for inflating the cuffs 26 and 30. Conventional valved ports 35 are employed at the free ends of the pilot tubes 28 and 32 for keeping the cuffs 26 and 30 inflated until it becomes necessary to extract the device 10 from the patient's respiratory passages.

The tube's distal end 16 terminates in an orifice 36 for ventilating the left lung from a point proximal to the branch 37 leading to the left upper lobe. A second orifice 38 is provided in a sidewall of the tube 12 between the cuffs 26 and 30 for ventilating the right lung. The lumen of the tube 12 is divided into left and right passageways by a septum 40, which extends from a point of attachment 42 at the proximal end 14 from which the tubular extensions 18 and 20 diverge to a point of attachment 44 on the interior wall of the tube 12 distal from the side orifice 38. Thus, the left lung can be ventilated through the left tubular extension 18 and the end orifice 36 via the left passageway, and the right lung can be ventilated through the right tubular extension 20 and the side orifice 38 via the right passageway.

The feature of the invention by which a dramatic improvement in performance is achieved will now be described with reference to FIGS. 2-7, like reference numerals designating like parts. The septum 40 comprises a thin flexible membrane of a suitable material such as plastic or rubber, the membrane having anterior and posterior attachments 46 and 48 to the tube 12 extending longitudinally along the interior of the tube 12 between the proximal attachment 42 and the distal attachment 44. The tube 12 is preferably cylindrical and thus appears circular in transverse section with the anterior and posterior attachments 46 and 48 defining left and right semicircular sidewalls 50 and 52, respectively. Because the septum 40 is flexible, it responds to unequal pressures on its opposed surfaces by moving toward the lower pressure side. In accordance with an important feature of the invention, the septum 40 has an anterior-posterior or transverse dimension approximately equal to one-half the circumference of the interior surface of the tube 12. Thus, the septum 40 has sufficient transverse slack such that it will be forced essentially flush against one of the sidewalls 50 or 52 by a differential pressure in the tube 12. It should be readily apparent, therefore, that virtually the entire cross-sectional area within the tube 12 can thereby be employed to ventilate the lung that corresponds to the higher pressure side of the tube 12.

Figure 3:
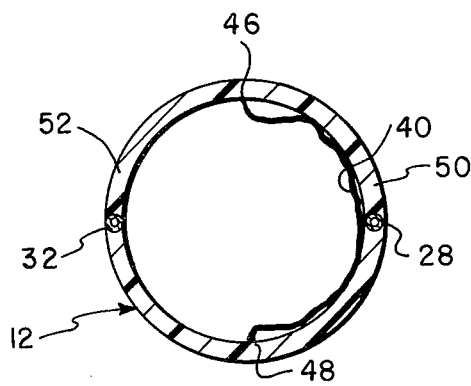
FIG. 3 is a greatly enlarged sectional view taken along line III—III of FIG. 2.
Figure 2:
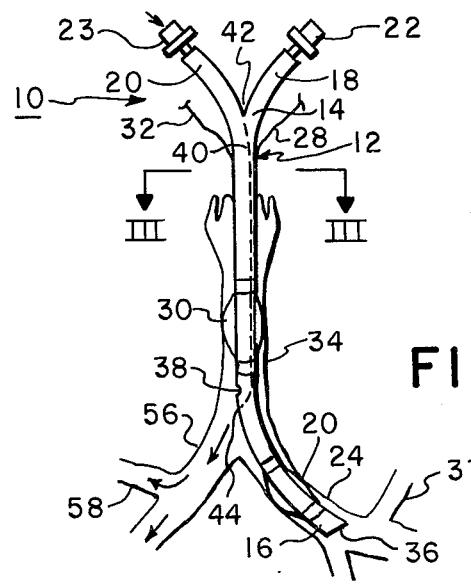
FIG. 2 is a diagrammatic front elevation depicting the device being employed to ventilate the patient's right lung alone.

FIGS. 2 and 3 depict the tube 12 during selective ventilation of the right lung. By way of example, assume that a conventional breaching machine is being employed and that the ventilating ports 22 and 23 are initially connected to separate catheters (not shown) leading to the breathing machine. The required pressure differential across the septum 40 for selective ventilation of the right lung can then be achieved simply by clamping the catheter connected to the left ventilating port 22 and then disconnecting the left ventilating port 22 therefrom thus bringing left tubular extension 18, left passageway and left lung into communication with the atmosphere and allowing the left lung to collapse. The right lung is then inflated by pumping a suitable gas into the right ventilating port 23 through the right passageway of the tube 12 and out the side orifice 38 as depicted by the arrows in FIG. 2. Deflation of the right lung occurs as a normal exhalation during a passive cycle of the breathing machine wherein gases flow outwardly in the opposite direction of the arrows. During the active cycle, the breathing machine pumps the gas into the right lung under a positive pressure which forces the septum 40 against the left sidewall 50 as seen in FIG. 3. Thus, the left passageway is essentially collapsed and the right passageway occupies roughly the entire cylindrical interior of the tube 12 between the right sidewall 52 and the septum 40.

Figure 5:
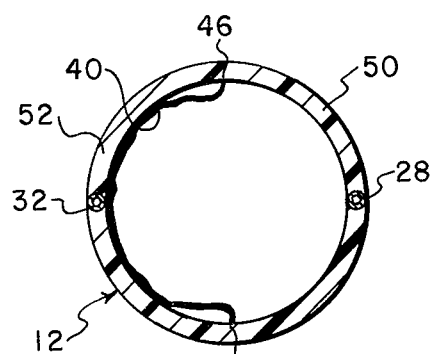
FIG. 5 is a greatly enlarged sectional view taken along line V—V of FIG. 4.
Figure 4:
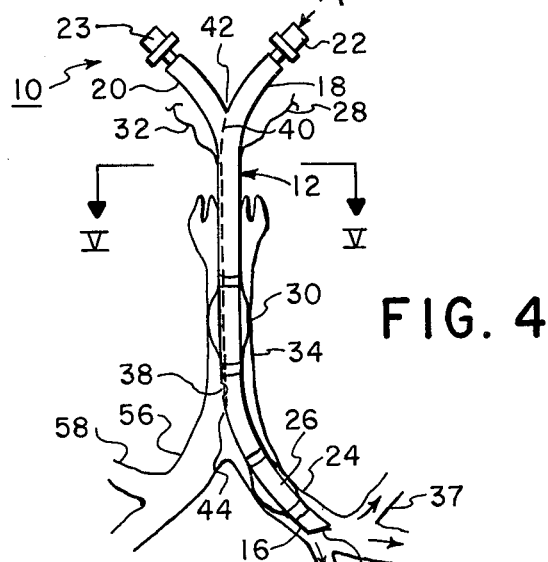
FIG. 4 is a diagrammatic front elevation depicting the device being employed to ventilate the patient's left lung alone.

It will be appreciated that the technique just described can be employed in similar fashion to selectively ventilate the left lung as depicted in FIGS. 4 and 5. Briefly, the catheter (not shown) connecting the right tubular extension 20 to the breathing machine is clamped and then the right tubular extension 20 is opened to the atmosphere. Thereafter, gas from the breathing machine will be pumped only into the left ventilating port 22 thus selectively ventilating only the left lung through the end orifice 36 as depicted by the arrows in FIG. 4, exhalation occurring in the direction opposite therefrom. As seen in FIG. 5, selective ventilation of the left lung alone under positive pressure forces the septum 40 against the right sidewall 52 so that the left passageway occupies roughly the entire cylindrical interior of the tube 12.

Figure 7:
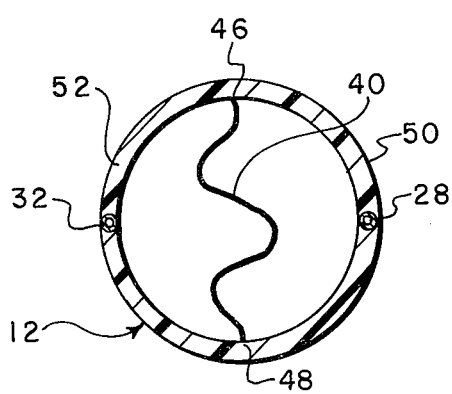
FIG. 7 is a greatly enlarged sectional view taken along line VII—VII of FIG. 6.
Figure 6:
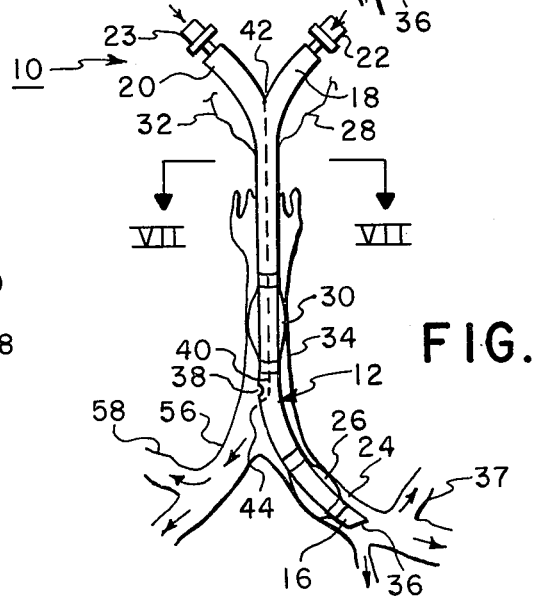
FIG. 6 is a diagrammatic front elevation depicting the device being employed to ventilate both lungs of the patient simultaneously.

When the surgical procedure requiring the selective ventilation of one lung alone is complete, the disconnected tubular extension 18 or 20 is reconnected to the catheter leading to the breathing machine to again ventilate both lungs simultaneously. Gasses are then forced under equal pressure into both lungs as depicted by the arrows in FIG. 6. Because the ventilating pressures are equal, the septum 40 returns to a middle or lax position to provide left and right passageways of roughly equal capacity as depicted in FIG. 7. It will be appreciated that the tube 12 functions equally well in conjunction with a manually operable breathing circuit in place of a breathing machine.

As mentioned above, the septum 40 preferably has a transverse dimension equal to one-half the circumference of the interior surface of the tube 12, which gives the septum 40 a convoluted appearance in the lax middle position. However, in accordance with a modified embodiment, an elastic septum with a transverse dimension equal to the inside diameter of the tube 12 can be provided so as to eliminate the convoluted condition when the septum is in the middle position. Such an elastic septum would divide the lumen of the tube 12 into two semicircular passageways when both lungs are being ventilated, thereby minimizing air resistance. Unfortunately, because the commonly employed breathing machines are essentially passive during the exhalation portion of the breathing cycle, such an elastic septum will also tend to move toward the middle position during exhalation when only one of the lungs is being ventilated. Since it is particularly important to provide as large a passageway as possible during exhalation so as to reduce the stress on the patient, any narrowing of the passageway due to the elasticity of the septum is undesirable. Thus, unless the particular breathing machine being employed is adapted to either prevent such narrowing of the passageway or to compensate for it in some suitable way, an elastic septum with a transverse dimension equal to the inside diameter of the tube 12 is less desirable than a septum, whether elastic or nonelastic, that has a transverse dimension approximately equal to one-half the circumference of the inside of the tube 12.

The tube 12 is preferably produced using conventional molding or extruding techniques. In accordance with one technique, the sidewalls 50 and 52 are formed separately by extruding a suitable polymeric material through a semicircular die orifice and then bonding the sidewalls and the septum 40 together to produce the cylindrical structure shown in the figures. Those skilled in the art of extruding rubbery polymers will appreciate that the pilot tubes 28 and 32 can readily be embedded in the sidewalls 50 and 52 during the extrusion process. Such embedding of pilot tubes has been employed in prior art devices and does not by itself constitute a novel feature of the present invention.

It will be appreciated that the device 10 of the present invention not only achieves improved performance but provides many additional advantages over similar devices of the prior art. For example, the outside diameter of the tube 12 can be made smaller compared to that of prior-art devices and yet still provide the same interior capacity during single-lung ventilation, thereby permitting employment of a device of this kind for the first time with small children. An additional advantage is that a fiber optic intubating device, which would otherwise be too large to be inserted through a device having a fixed septum, can be passed down to the tube's distal end 16, the flexible septum 40 being pushed to one side in the process. Such use of a fiber optic device enables accurate initial positioning of the tube 12 in the respiratory passages by direct vision. Likewise, a suction catheter having a larger diameter than could otherwise be employed with a fixed septum device can be passed down the tube 12 to facilitate removal of unwanted fluids.

The above described device 10 can be employed in various intrathoracic operations with the exception of a left pneumonectomy in which the distal end 16 of the tube 12 would interfere with the severing of the left main stem bronchus 24. Accordingly, the present invention contemplates a modified embodiment (not shown) of the device 10 having a distal end adapted to be inserted into the right main stem bronchus 56 so as to permit severing of the proximal end of the left main stem bronchus 24. Because the branch 58 to the right upper lobe is relatively close to the distal end of the trachea 34, a modified bronichal cuff can be provided with a port hole adapted to ventilate the right upper lobe through the branch 58 while maintaining a gaseous seal within the right main stem bronchus 56.

Although a preferred embodiment and modifications thereof have been described in detail, it is to be understood that additional modifications and substitutions can be made and various alternative embodiments produced in accordance with the invention without departing from the spirit and scope thereof as defined by the appended claims.

What is claimed is:

1. A respiratory ventilating device for conducting gaseous materials under slight gaseous pressure differential to and from the lungs of a patient separately or simultaneously, comprising:

an elongated flexible tube adapted to extend through the patient's trachea to a point within the bronchus of one lung, said tube having walls forming a generally cylindrical interior surface, first means disposed about said tube for forming a gaseous seal in said bronchus, second means disposed about said tube for forming a gaseous seal in the trachea, said tube having a first opening distal to both said seal means and a second opening between said first seal means and second seal means, a thin flexible membrane dividing the interior of said tube into first and second isolated longitudinal passageways, said membrane being sufficiently flexible to respond to differences in pressures of the gasses conducted by said longitudinal passageways by moving toward the passageway corresponding to the lower gaseous pressure, said membrane having a lax transverse dimension approximately equal to one half of the interior surface of said tube and having a thickness dimension much smaller than the thickness of the walls of the tube whereby the passageway corresponding to the higher pressure will occupy substantially the entire cylindrical interior of the tube, said first longitudinal passageway having a distal end communicating with said first opening, said second longitudinal passageway having a distal end communicating with said second opening, said first and second ventilating ports communicating respectively with the proximal ends of said first and second longitudinal passageways.

2. The device of claim 1 wherein said membrane has first and second longitudinal attachments to said tube disposed approximately 180° apart on said interior surface.

3. The device of claim 1 or 2 wherein said membrane is sufficiently thin and flexible that it can remain in a convoluted middle position in the tube to provide the first and second longitudinal passageways with approximately equal capacities during simultaneous ventilation of both lungs using approximately equal gaseous pressures in the first and second longitudinal passageways.

* * * * *